US012042666B2

(12) United States Patent
Broer et al.

(10) Patent No.: US 12,042,666 B2
(45) Date of Patent: Jul. 23, 2024

(54) PHOTOTHERAPY DEVICE INCLUDE TWO OR MORE LIGHT PADS AND A FLEXIBLE GARMENT

(71) Applicant: LUMITEX, INC., Strongsville, OH (US)

(72) Inventors: Peter Broer, Bratenahl, OH (US); David G. Felty, Parma, OH (US); Brian Andrich, Strongsville, OH (US); Vedang Kothari, Cleveland, OH (US)

(73) Assignee: Lumitex, Inc.

( * ) Notice: Subject to any disclaimer, the term of this patent is extended or adjusted under 35 U.S.C. 154(b) by 471 days.

(21) Appl. No.: 16/979,223

(22) PCT Filed: Mar. 12, 2019

(86) PCT No.: PCT/US2019/021739
§ 371 (c)(1),
(2) Date: Sep. 9, 2020

(87) PCT Pub. No.: WO2019/178017
PCT Pub. Date: Sep. 19, 2019

(65) Prior Publication Data
US 2020/0406056 A1    Dec. 31, 2020

Related U.S. Application Data

(60) Provisional application No. 62/643,191, filed on Mar. 15, 2018.

(51) Int. Cl.
*A61N 5/06* (2006.01)
*A41D 1/00* (2018.01)

(52) U.S. Cl.
CPC ........... *A61N 5/0621* (2013.01); *A41D 1/002* (2013.01); *A61N 2005/063* (2013.01);
(Continued)

(58) Field of Classification Search
CPC . A61B 5/6833; A61B 5/0022; A61B 5/02055; A61B 5/112; A61B 5/14542;
(Continued)

(56) References Cited

U.S. PATENT DOCUMENTS

| 6,596,016 B1* | 7/2003 | Vreman | A61N 5/0621 |
| | | | 128/903 |
| 2004/0143307 A1* | 7/2004 | Williams | A61N 5/0621 |
| | | | 607/88 |

(Continued)

FOREIGN PATENT DOCUMENTS

WO    01/14012    3/2001

OTHER PUBLICATIONS

International Search Report and Written Opinion for corresponding International Patent Application No. PCT/US2019/021739 mailed on Jan. 21, 2020.

*Primary Examiner* — Gary Jackson
*Assistant Examiner* — Ranjani Mari Sundaresan
(74) *Attorney, Agent, or Firm* — Renner, Otto, Boisselle & Sklar, LLP

(57) ABSTRACT

A phototherapy device for delivering light emitted by a light source to an infant. The phototherapy device includes two or more light pads configured to be optically connected to a light source via a connector. Light emitted by the light source is received by the connector and propagated through the connector to the light pads. The phototherapy device also includes a flexible garment configured to maintain the position of the pads on a front and back of an infant.

20 Claims, 16 Drawing Sheets

(52) U.S. Cl.
CPC ............. *A61N 2005/0632* (2013.01); *A61N 2005/0645* (2013.01); *A61N 2005/0647* (2013.01); *A61N 2005/0651* (2013.01); *A61N 2005/0665* (2013.01)

(58) Field of Classification Search
CPC ..... A61B 5/165; A61B 5/4818; A61B 5/4875; A61B 5/681; A61B 5/7264; A61B 5/742; A61B 7/04; A61B 5/02405; A61B 5/0245; A61B 5/0816; A61B 2503/04; A61B 2503/08; A61B 2503/40; A61B 2560/0443; A61B 2562/0219; A61B 2560/0412; A61B 2560/045; A61B 5/0205; A61B 5/00; G16H 40/67
See application file for complete search history.

(56) References Cited

U.S. PATENT DOCUMENTS

| | | | |
|---|---|---|---|
| 2006/0038192 A1* | 2/2006 | Williams | A61N 5/06 257/98 |
| 2010/0270924 A1* | 10/2010 | Kaminska | H10K 59/00 257/98 |
| 2011/0176326 A1* | 7/2011 | Stephan | G02B 6/0008 362/555 |
| 2015/0362828 A1* | 12/2015 | Patel | A61B 1/0669 348/75 |
| 2016/0315448 A1* | 10/2016 | Rosenberg | H01L 23/3672 |
| 2017/0118838 A1* | 4/2017 | Williams | H05K 3/027 |

\* cited by examiner

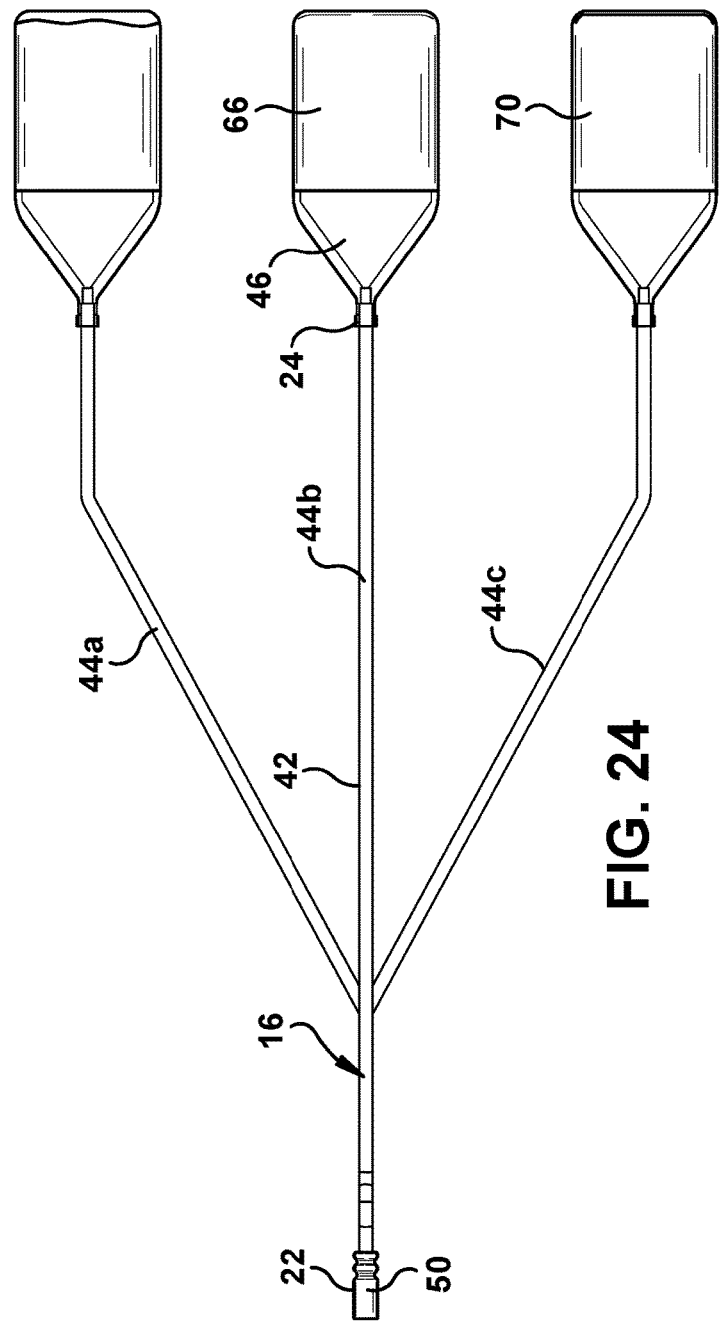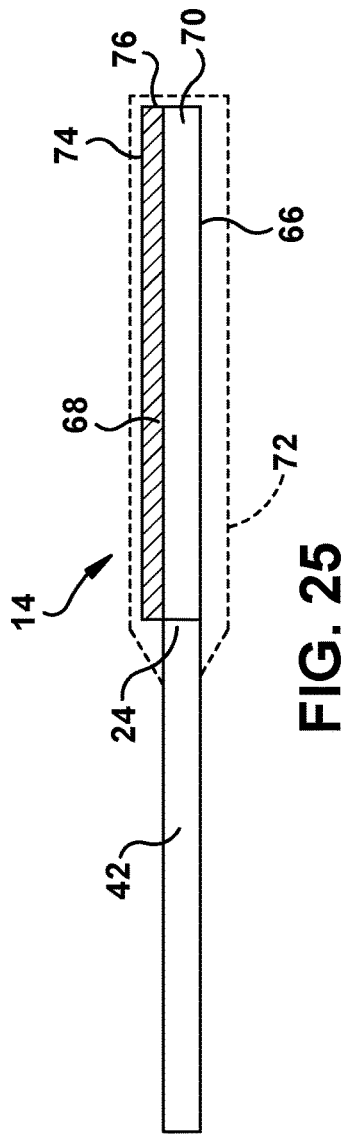
FIG. 24
FIG. 25

PHOTOTHERAPY DEVICE INCLUDE TWO OR MORE LIGHT PADS AND A FLEXIBLE GARMENT

This application is a national phase of International Application No. PCT/US2019/021739 filed Mar. 12, 2019 which claims benefit of U.S. Provisional Application No. 62/643,191 filed on Mar. 15, 2018 and published in the English language.

TECHNICAL FIELD

The present disclosure relates generally to a phototherapy device and system for delivering light to the front and back of an infant's torso.

BACKGROUND

Phototherapy has long been used to treat newborn infants for various maladies including jaundice. Jaundice is caused by a buildup of bilirubin in the blood of infants. Exposing the infant's skin to certain types of light will quickly reduce the bilirubin to a safe level.

A common problem in the treatment of jaundice, especially in full-term babies, is the inability to swaddle or nurse the baby during treatment. Because treating jaundice typically involves exposing a baby's skin to overhead lights (the light converting bilirubin to another molecule that kidneys typically can filter), the baby's trunk is exposed and unwrapped. Often when a baby is not tucked or swaddled, the baby panics, flails arms, and cries. This often causes a parent or nurse to end treatment prematurely, at the risk of jaundice levels remaining elevated.

SUMMARY

In a full-term nursery, it would be preferably to wrap babies fully in light while at the same time restraining movement of the baby's arms, making babies more comfortable in the normal fetal or wrapped position (also called swaddled). By maintaining a position of light emitters relative to the baby, it is also possible to prevent the need for babies to wear protective eye patches.

It is possible to swaddle a baby during phototherapy by using multiple flexible light emitting pads inserted in a flexible garment. It is possible to perform phototherapy while at the same time swaddling the infant by providing light to the light emitting pads using external light sources capable of providing enough light to expose the full circumference of a baby's torso at an adequate dosage for effective treatment.

By using multiple light emitting pads 14, it is possible to achieve full 360-degree coverage of an infant's body, which has previously only been accomplished with double phototherapy (e.g., one device overhead and one fiber optic pad beneath). The use of a branching connector 16 also makes it possible to perform phototherapy treatment using a single light source.

The present disclosure provides a phototherapy device including two or more light pads and a flexible garment to maintain the position of the pads on a front and back of an infant. The phototherapy device allows an infant to be swaddled while the infant simultaneously receives phototherapy treatment on his/her front and back.

The present disclosure also provides a phototherapy device including two or more pads that are optically connected via a branching connector to a single output port of a light source.

The present disclosure additionally provides an optical connector having a magnetic material for maintaining a connection with a light source and a non-magnetic material thermally connected to the magnetic material and acting as a heat sink.

The present disclosure further provides a light source including an inductor positioned to absorb electromagnetic interference generated by electrical components.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

FIG. 24 is a schematic drawing of a connector and the light emitting pads.

FIG. 25 is a schematic drawing of the light emitting pads.

DETAILED DESCRIPTION

Figure 1:
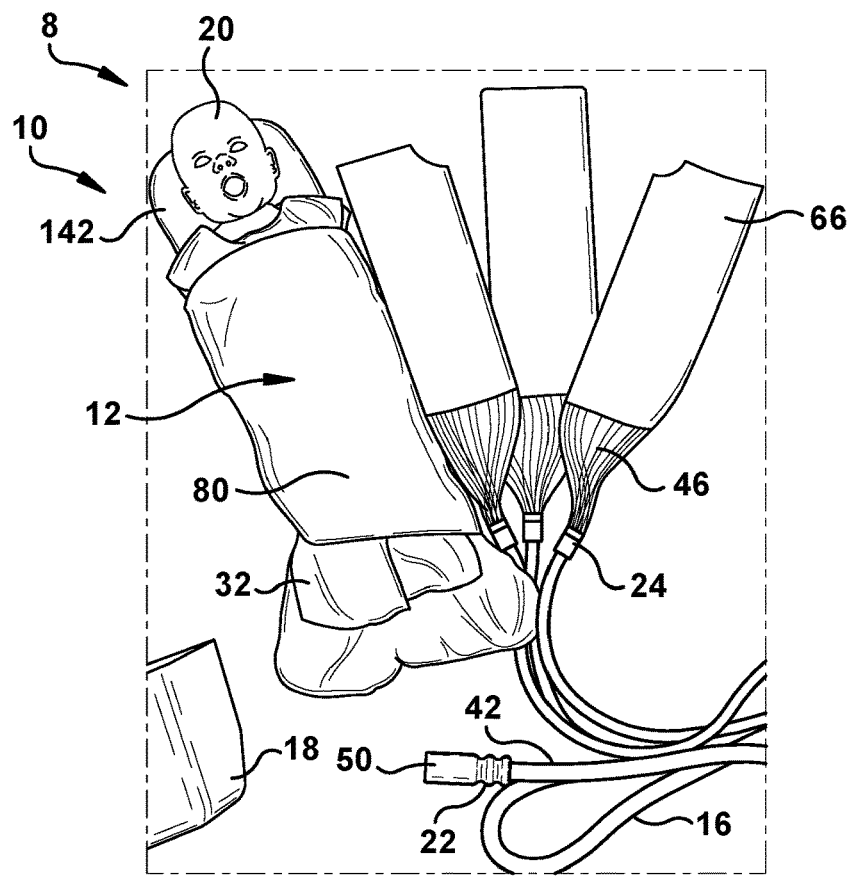
FIG. 1 is an exemplary embodiment of a phototherapy system showing light emitting pads located outside of a flexible garment.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

The present invention provides a phototherapy device for delivering light emitted by a light source to an infant. The phototherapy device includes two or more light pads configured to be optically connected to a light source via a connector.

Light emitted by the light source is received by the connector and propagated through the connector to the light pads. The phototherapy device also includes a flexible garment configured to maintain the position of the pads on a front and back of an infant.

Figure 2:
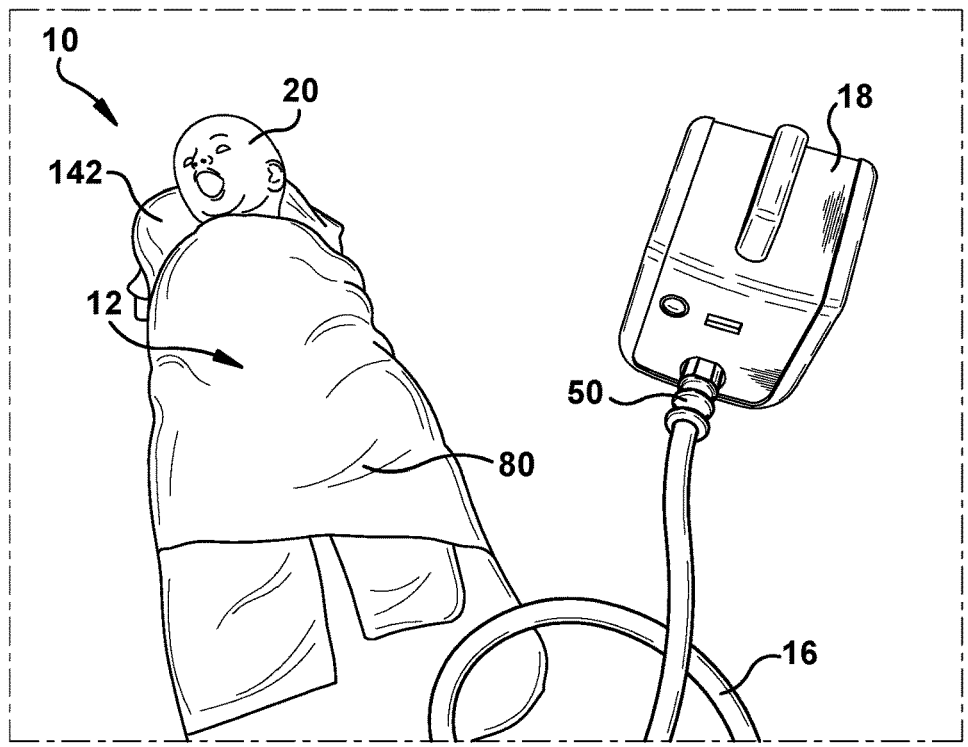
FIG. 2 is an exemplary embodiment of the phototherapy system of FIG. 1 with the light emitting pads located inside pockets of the flexible garment.

Turning to FIGS. 1 and 2, an exemplary phototherapy system 8 is shown including a phototherapy device 10 and a light source 18. The phototherapy device 10 includes a flexible garment 12 and at least two discrete light emitting pads 14. The light emitting pads are configured to be optically connected via a connector 16 to the light source 18. The light emitting pads 14 are maintained in position relative to an infant 20 by the flexible garment 12.

The light emitting pads 14 are configured to be optically connected to the light source 18 via the connector 16. Light emitted by the light source 18 is received at a proximal end 22 of the connector 16. This light is propagated through the connector 16 to the light emitting pads 14, where the light is emitted by the light emitting pads 14.

With continued reference to FIG. 1, the light emitting pads 14 include at least one front light emitting pad 14a and a back light emitting pad 14b. For example, the phototherapy device 10 may include three light emitting pads 14: a front left light emitting pad 14a1, a front right light emitting pad 14a2, and a back light emitting pad 14b.

Figure 3:
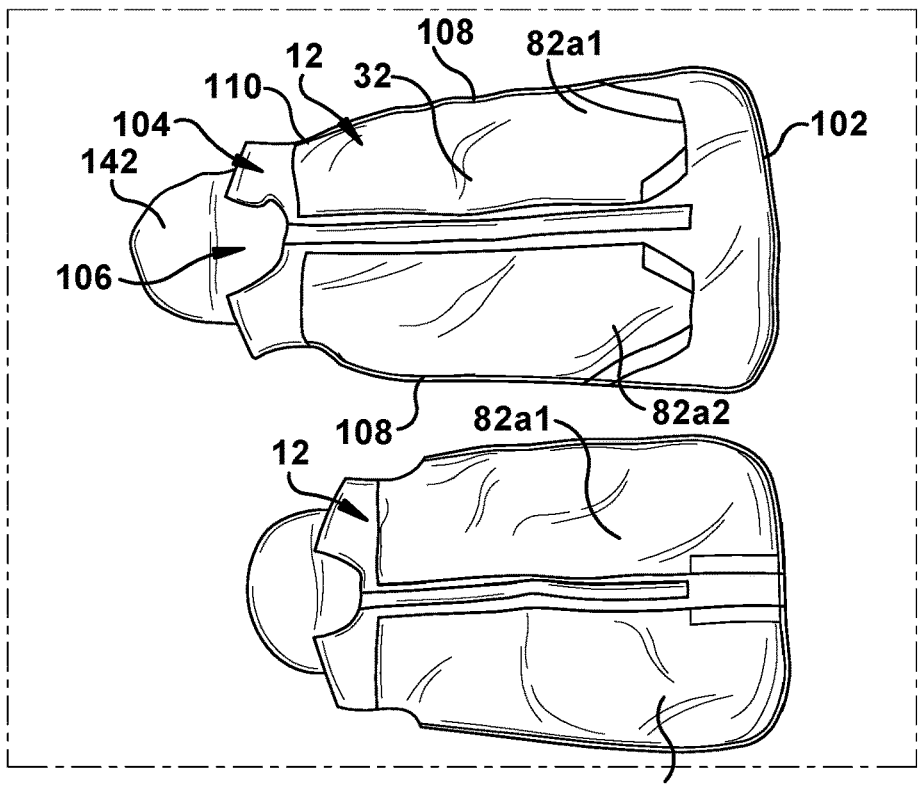
FIG. 3 shows a front surface of two flexible garments of different sizes.
Figure 4:
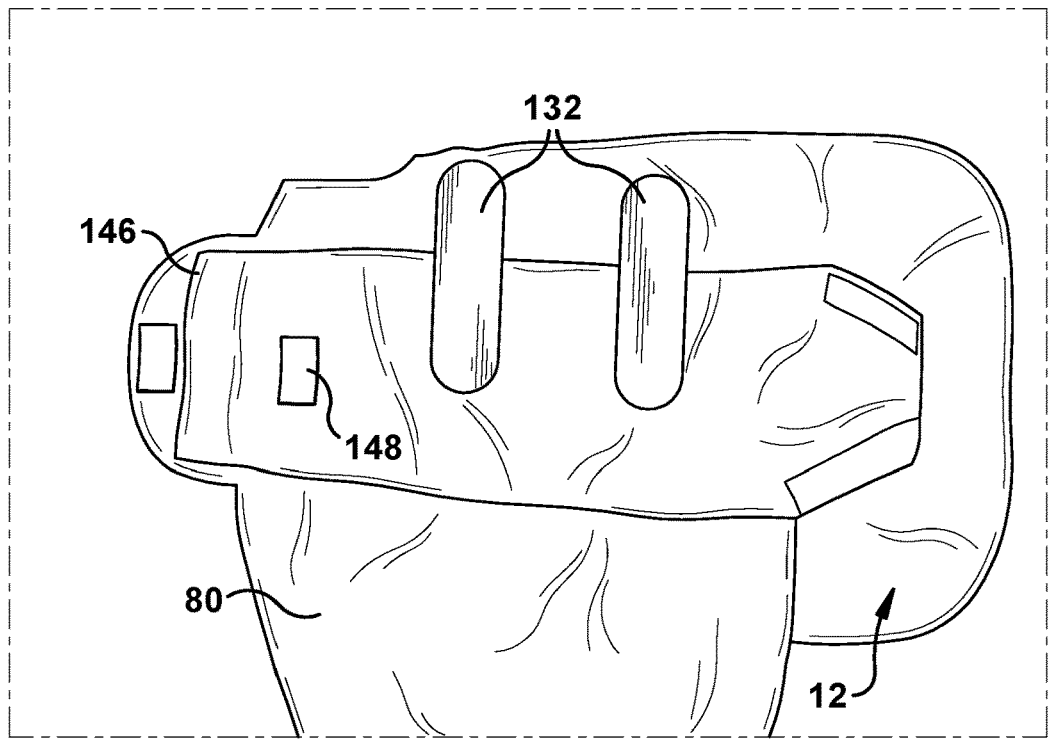
FIG. 4 shows a back side of an exemplary flexible garment.

Turning to FIGS. 3 and 4, two flexible garments 12 of different size are shown. The flexible garment 12 is configured to receive the infant 20 and the light emitting pads 14. For example, the flexible garment 12 may be a flexible cover configured to wrap around the infant 20. The flexible garment 12 may be made from any suitable material. For example, the flexible garment 12 may be made from a blend of cotton, nylon, or other suitable polymers.

As an example, the flexible garment 12 may be made from two or more layers of a woven fabric, or if disposable, two or more layers of a spun woven paper-like material. The portion of the flexible garment 12 that contacts an infant's skin when the infant is received in the flexible garment 12 may be made out of a soft fabric-like material that is relatively light transmissive. For example, the flexible garment 12 may be made from a first fabric layer (configured to contact an infant's skin) that is relatively thin and/or loosely woven or the fabric fibers themselves can be relatively transparent or translucent to permit light to pass therethrough. A second fabric layer located opposite the first fabric layer may be quilted to provide added softness. Further, a fill material may be located between the first and second fabric layer and act as insulation to help the infant retain warmth.

Figure 5:
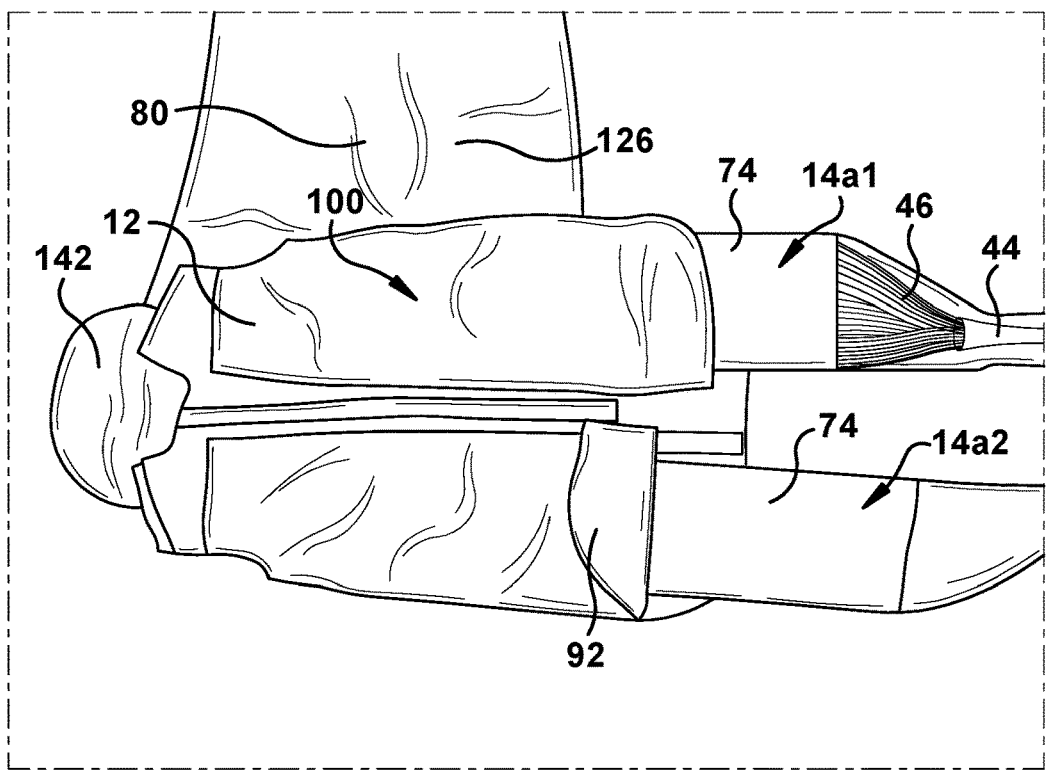
FIGS. 5 and 6 show the light emitting pads located partially within the pockets of the flexible garment.
Figure 6:
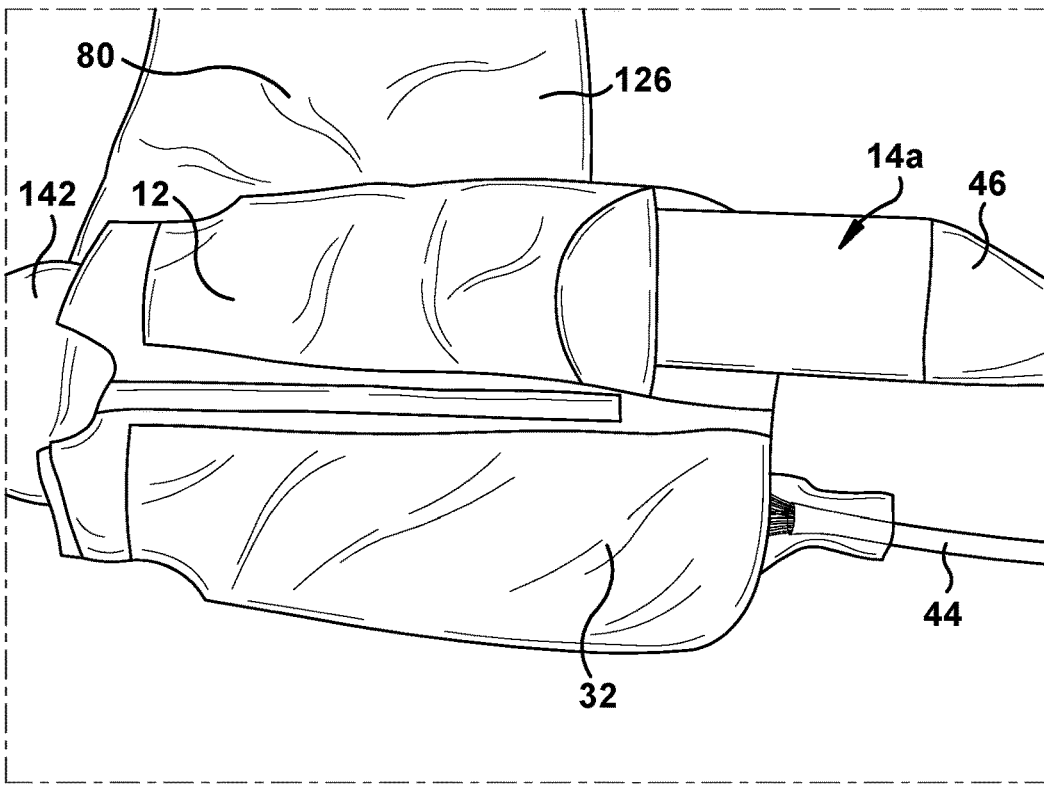

As shown in FIGS. 5 and 6, the flexible garment 12 is configured to maintain the position of the at least two pads 14 relative to the infant 20 (e.g., so that the infant receives phototherapy over the front and back of their torso simultaneously. The flexible garment 12 includes a front side 32 and a back side 34. The front side 32 of the flexible garment 12 is configured to be located adjacent a chest of the infant 20 when the infant 20 is received in the flexible garment 12. Similarly, the back side 34 of the flexible garment 12 is configured to be located adjacent a back of the infant 20 when the infant 20 is received in the flexible garment 12.

A position of the front light emitting pad 14a is maintained by the garment on the front side 32 of the flexible garment 12 when the front light emitting pad 14a is received by the flexible garment 12. Similarly, a position of the back light emitting pad 14b is maintained by the garment on the back side 34 of the flexible garment 12 when the back light emitting pad 14b is received by the flexible garment 12. When both the infant 20 and the at least two pads 14 are received by the flexible garment 12, light emitted by the light emitting pads 14 illuminates a torso of the infant 20.

Figure 7:
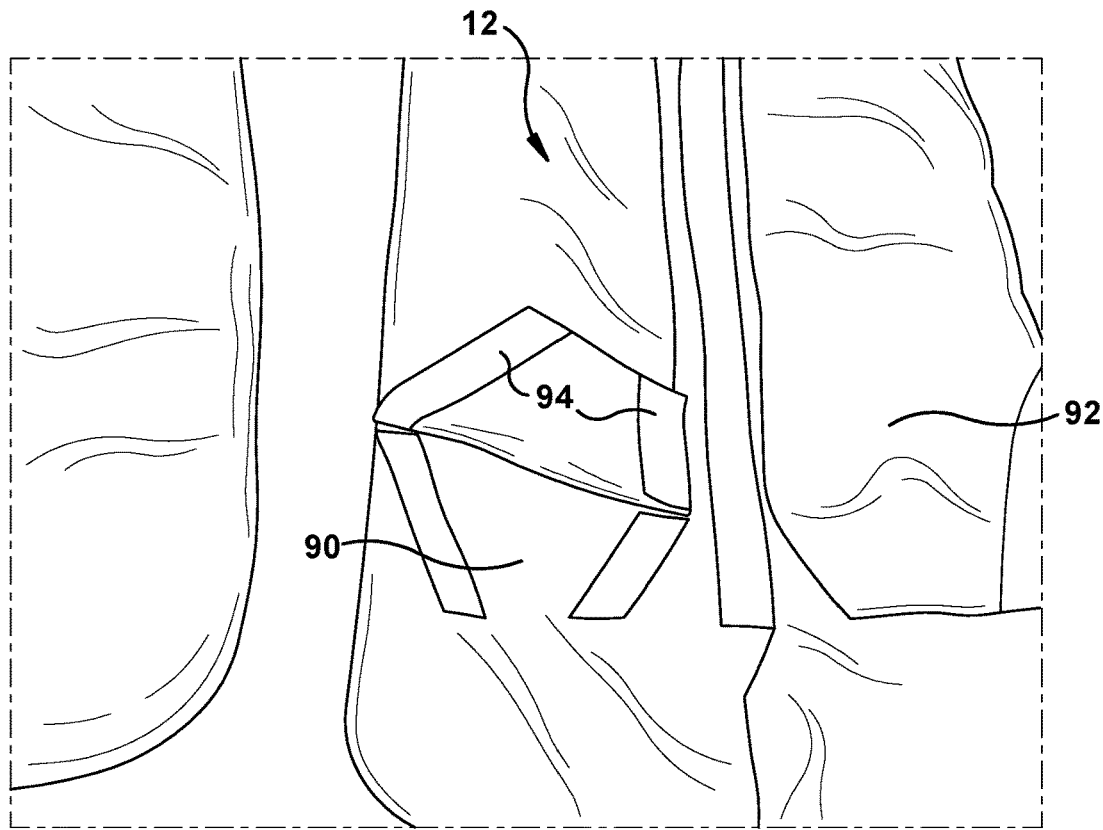
FIGS. 7-9 show pockets of the flexible garment and a fastening mechanism for closing the pocket.
Figure 8:
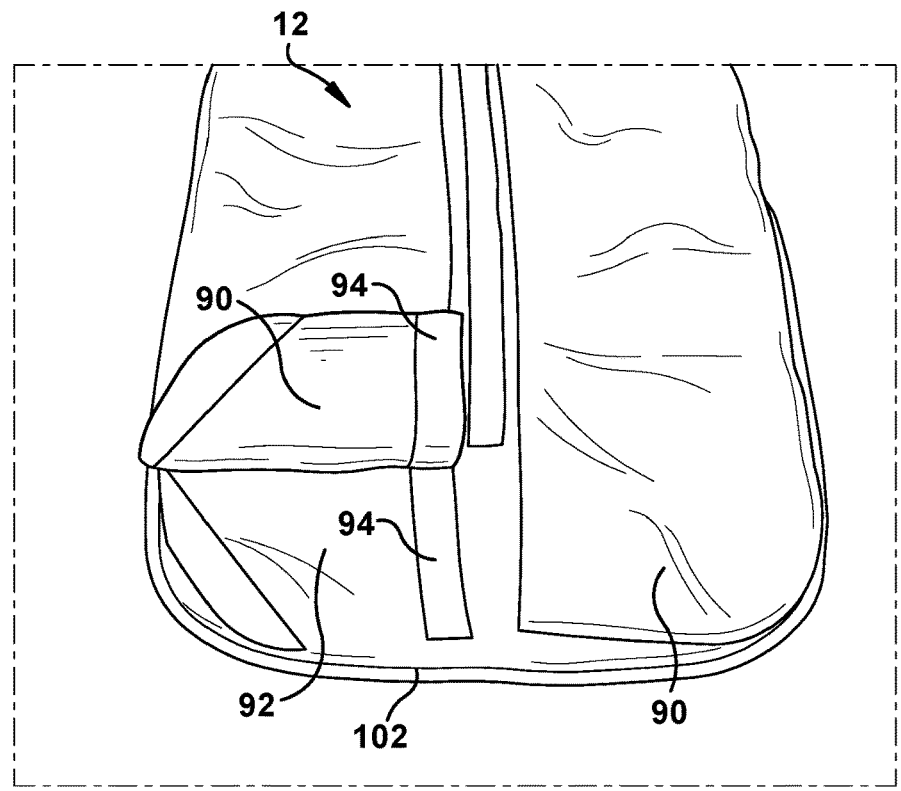
Figure 9:
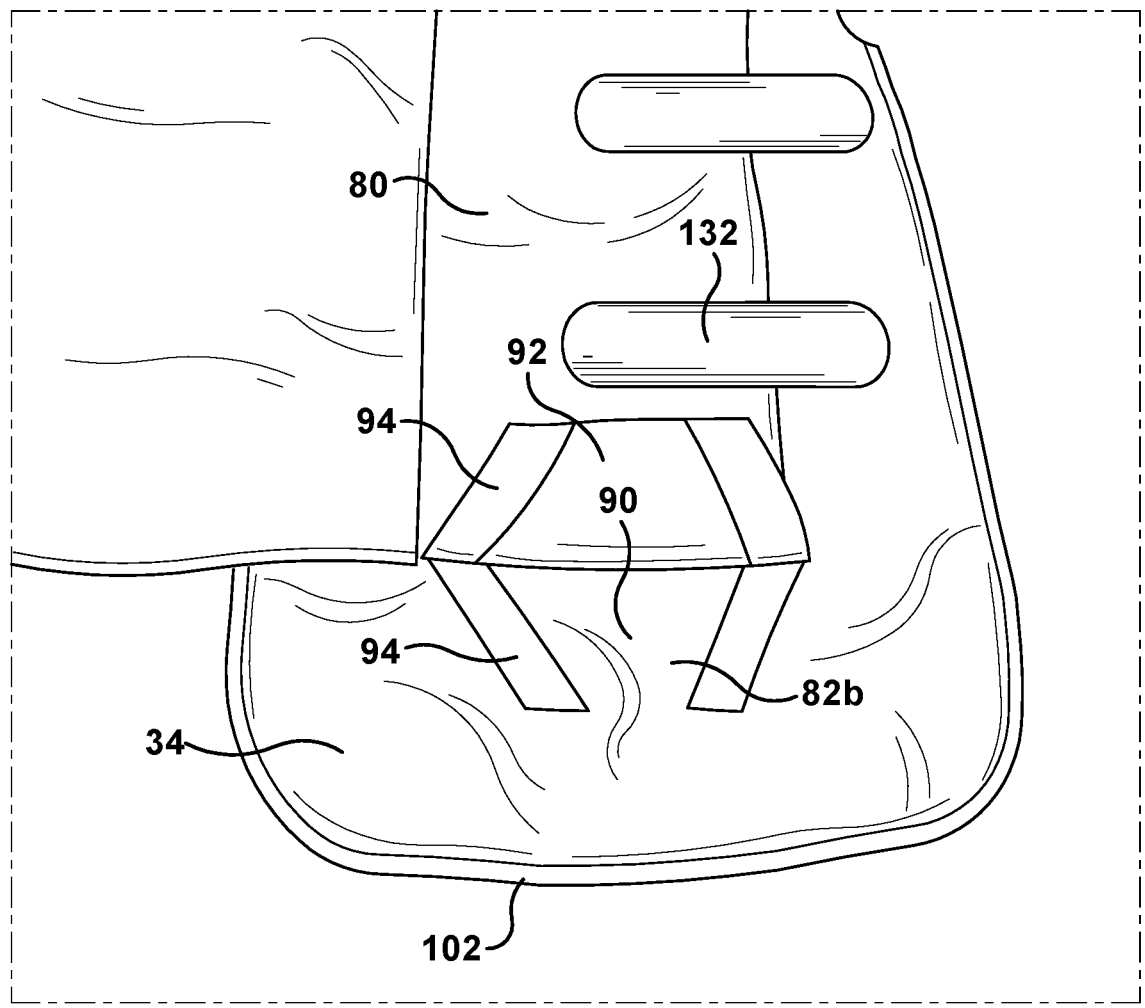

Turning to FIGS. 7-9, the position of the light emitting pads 14 may be maintained by pockets 82 in the flexible garment 12. For example, the flexible garment 12 may include at least two pockets 82 including a front pocket 82a located on the front side 32 of the flexible garment 12 and a back pocket 82b located on the back side 34 of the flexible garment 12. Each of the pockets 82 may be configured to receive and maintain a position of at least one of the light emitting pads 14. That is, the position of the front light emitting pad 14a may be maintained by the front pocket 82a and the position of the back light emitting pad 14b may be maintained by the back pocket 82b.

Each pocket 82 may include an outer wall 90 and an inner wall 92 located opposite the outer wall 90. The inner wall 92 may be positioned between the infant 20 and the at least one light emitting pad 14 received by the pocket 82. To allow light from the light emitting pad 14 to reach the infant, the inner wall 92 may be at least partially transparent to light emitted by the at least one light emitting pad 14 received by the pocket 82. For example, the inner wall 92 may be at least 50%, 70%, 85%, or 90% transparent to light having a wavelength of 450 nm.

To reduce the amount of light emitted by the light emitting pads 14 that escapes from the flexible garment 12 in a direction away from the infant 20, the outer wall 90 may be at least partially opaque to light emitted by the at least one light emitting pad 14 received by the pocket 82. For example, the outer wall 90 may be at least 50%, 70%, 85%, or 90% opaque to light having a wavelength of 450 nm.

Each pocket 82 may include a fastening mechanism 94 to maintain the position of the light emitting pad 14 received in the respective pocket 82. As an example, two pockets with differently oriented fastening mechanisms 94 are shown in FIGS. 7-9. In FIGS. 7 and 9, a pocket 82 with a tapered opening is shown on the front side 32 and the back side 34 of the flexible garment 12 respectively. In FIG. 8, a pocket 82 with a non-tapered opening is shown on the front side 32 of the flexible garment 12. A tapered pocket may reduce the chance that a light emitting pad 14 unintentionally comes out of the pocket 82. It may be easier to insert and remove a light emitting pad 14 from a non-tapered pocket.

With continued reference to FIGS. 7-9, the flexible garment 12 may include three pockets 82: a front left pocket

82*a*1 located on the front left side of the flexible garment 12, a front right pocket 82*a*2 located on the front right side of the flexible garment 12, and a back pocket 82*b* located on the back side 34 of the flexible garment 12. When the light emitting pads 14 are received by the flexible garment 12, a position of a front left light emitting pad 14*a*1 may be maintained by the garment on the front left side of the flexible garment 12 by the front left pocket 82*a*1, a position of the front right light emitting pad 14*a*2 may be maintained by the garment on the front right side of the flexible garment 12 by the front right pocket 82*a*2, and a position of the back light emitting pad 14*b* may similarly be maintained by the garment on the back side 34 of the flexible garment 12 by the back pocket 82*b*.

Figure 10:
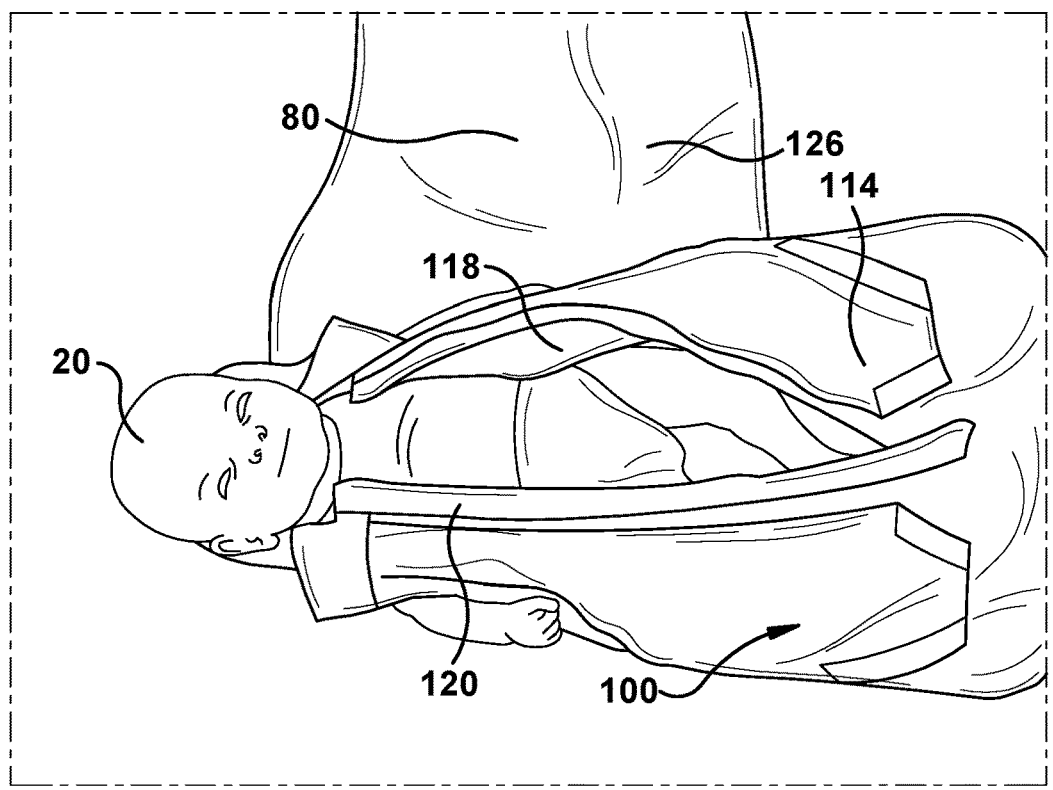
FIGS. 10 and 11 show an infant located with the flexible garment.
Figure 11:
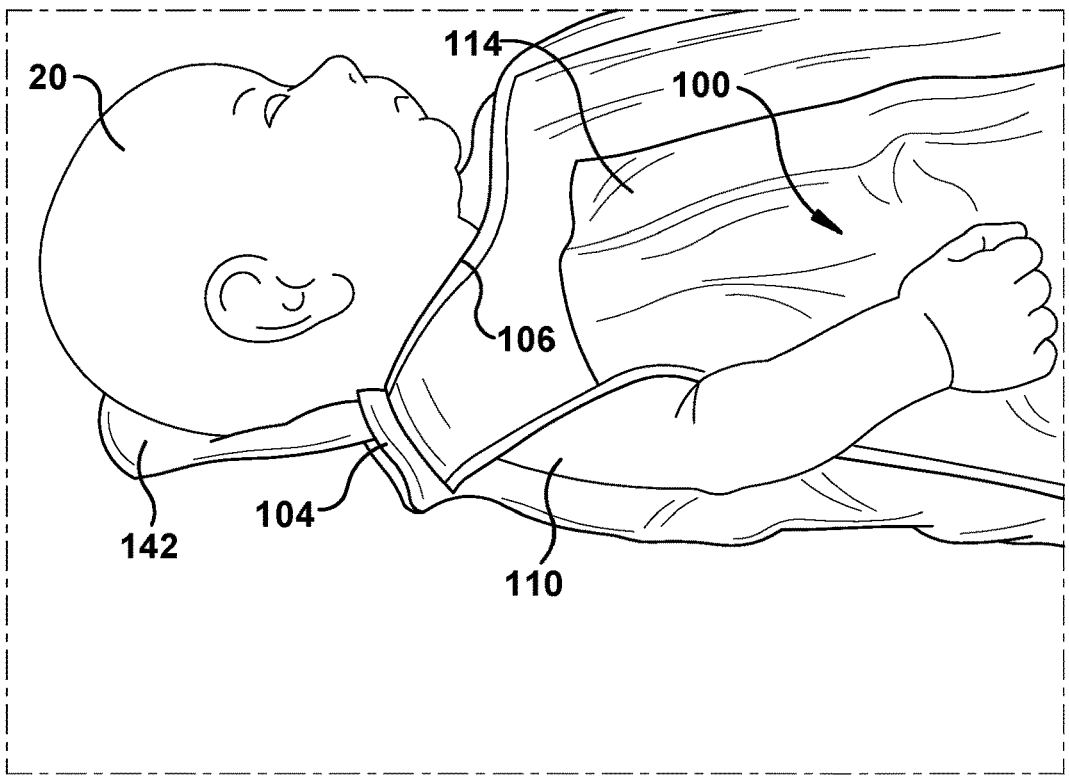

Returning to FIG. 3, the flexible garment 12 may include a sack 100 having a closed bottom edge 102, a partially closed top 104, and two partially closed sides 108. As shown in FIGS. 10 and 11, the partially closed top 104 includes a hole 106 through which a neck of the infant 20 extends when the infant 20 is received in the flexible garment 12. Similarly, the two partially closed sides 108 including arm holes 110 through which arms of the infant 20 extend when the infant 20 is received in the flexible garment 12.

Figure 12:
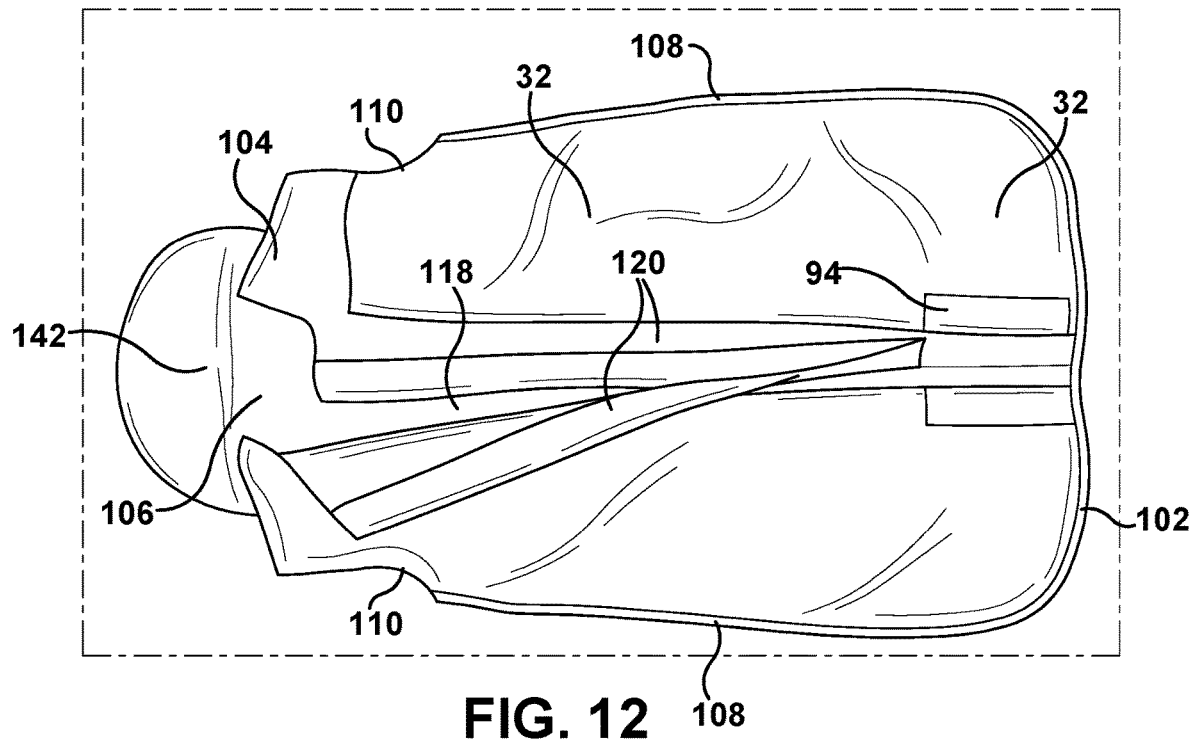
FIGS. 12 and 13 show a sack of the flexible garment including a head piece.
Figure 13:
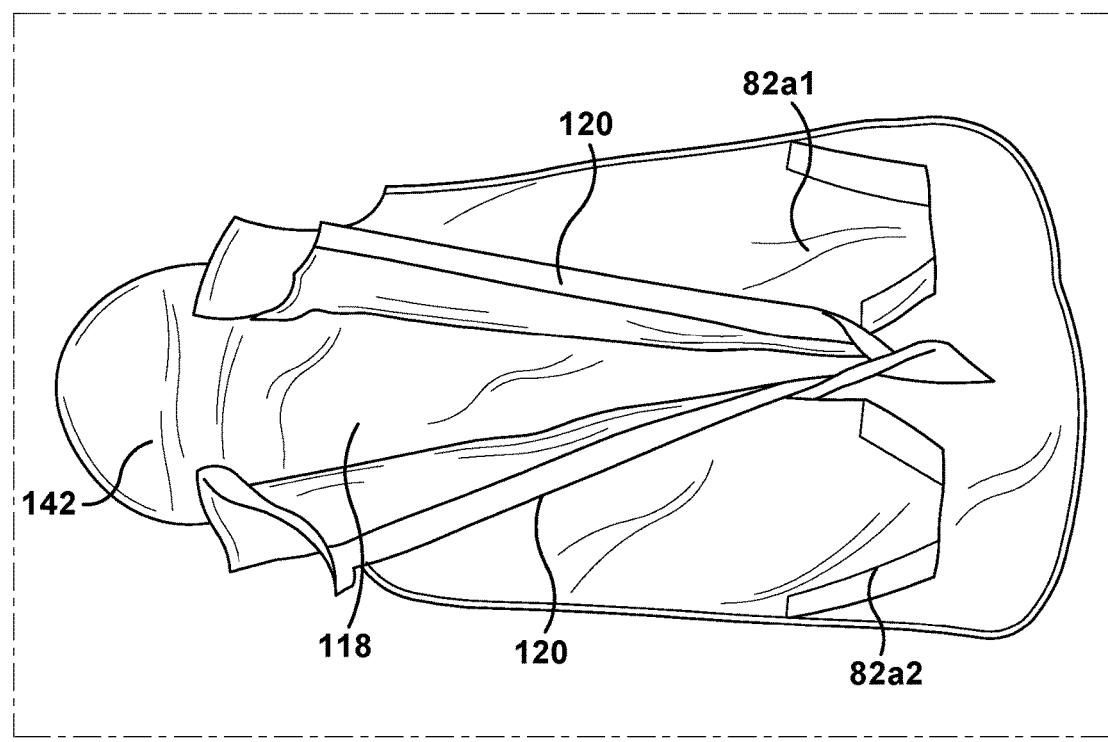
Figure 14:
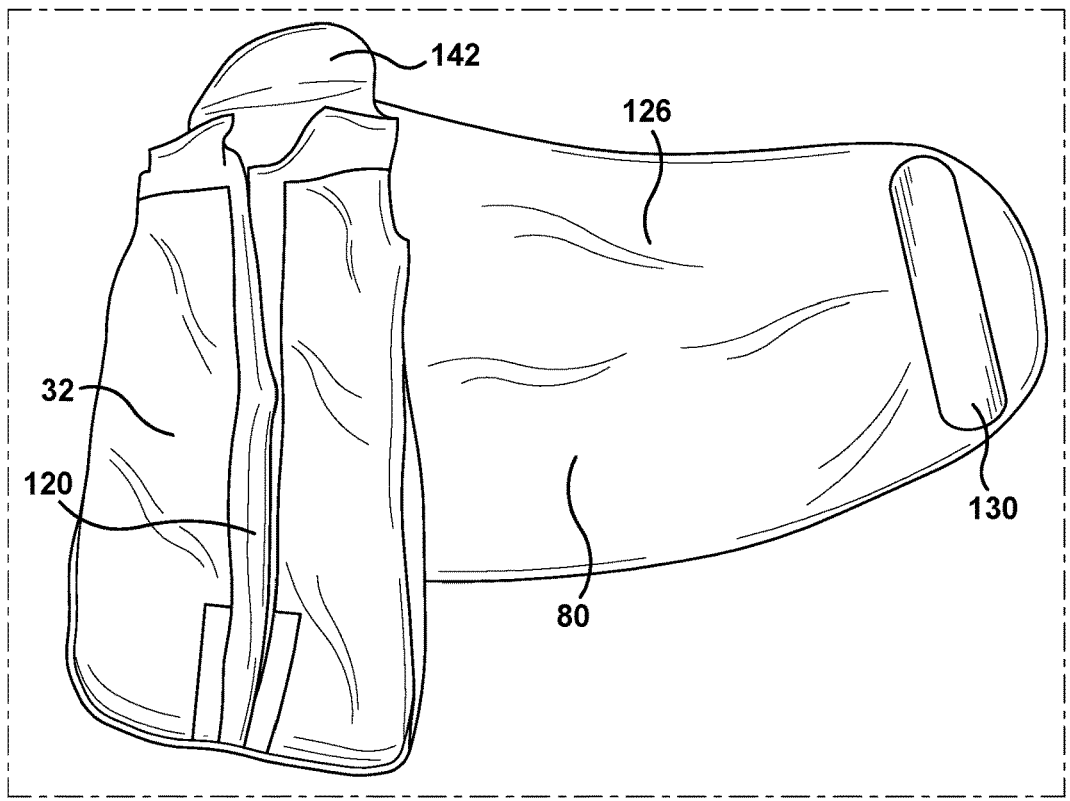
FIGS. 14 and 15 show the flexible garment including a wrap.
Figure 15:
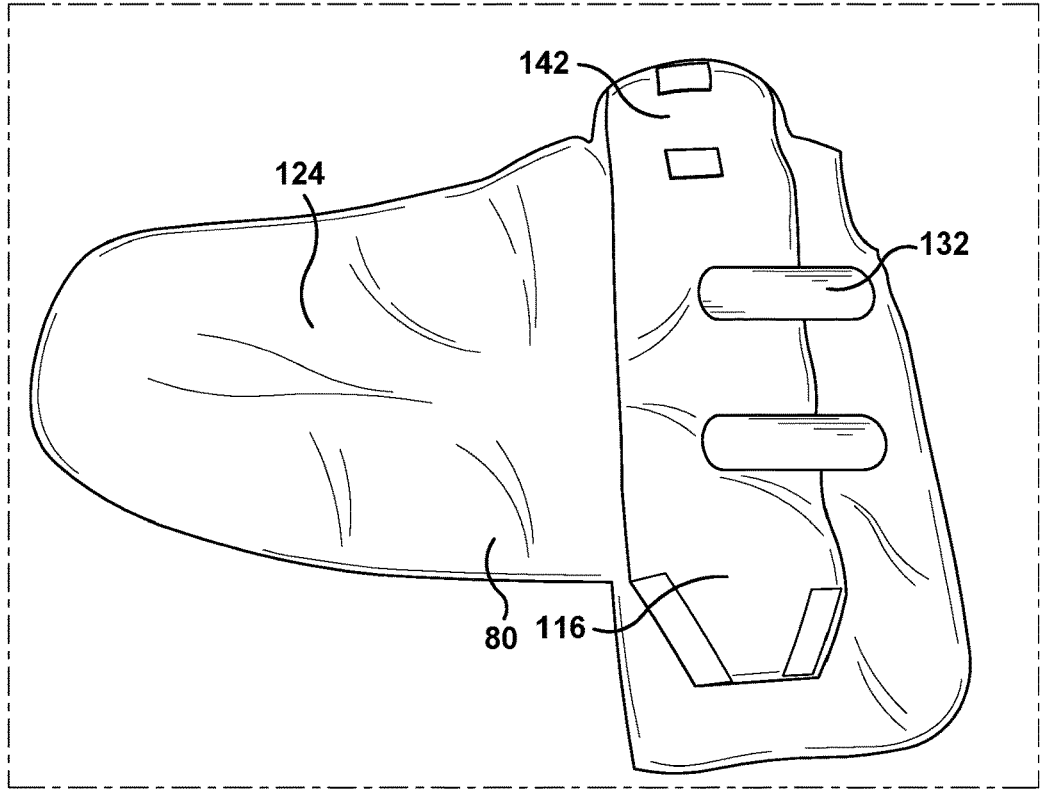
Figure 16:
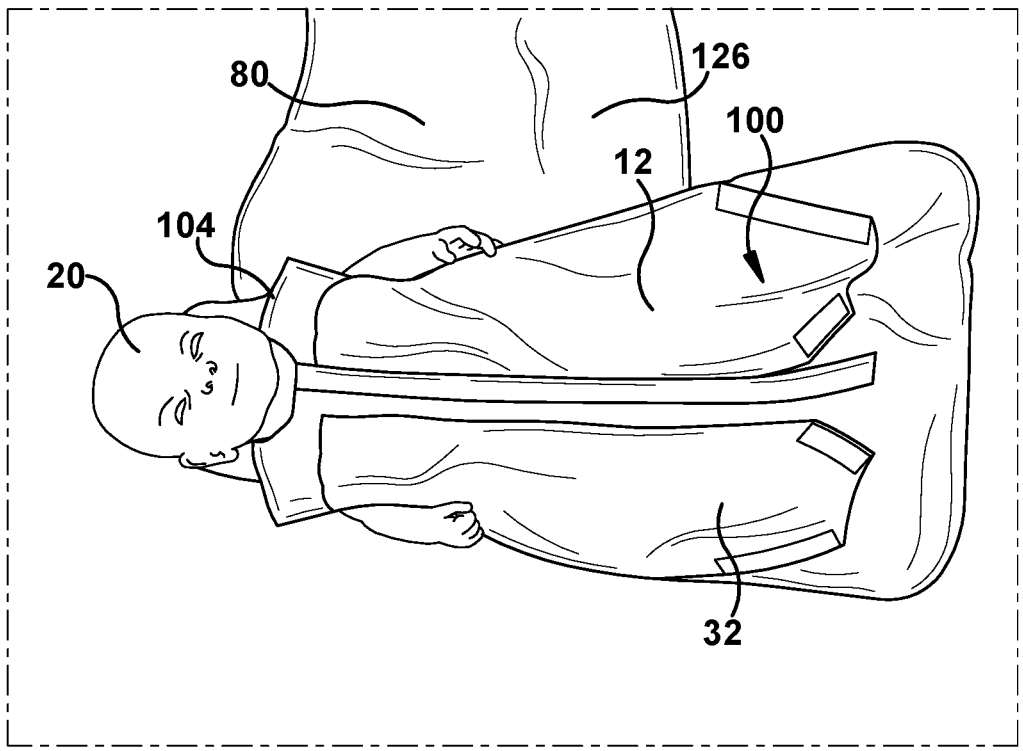
FIGS. 16 and 17 show an infant being swaddled in the flexible garment.
Figure 17:
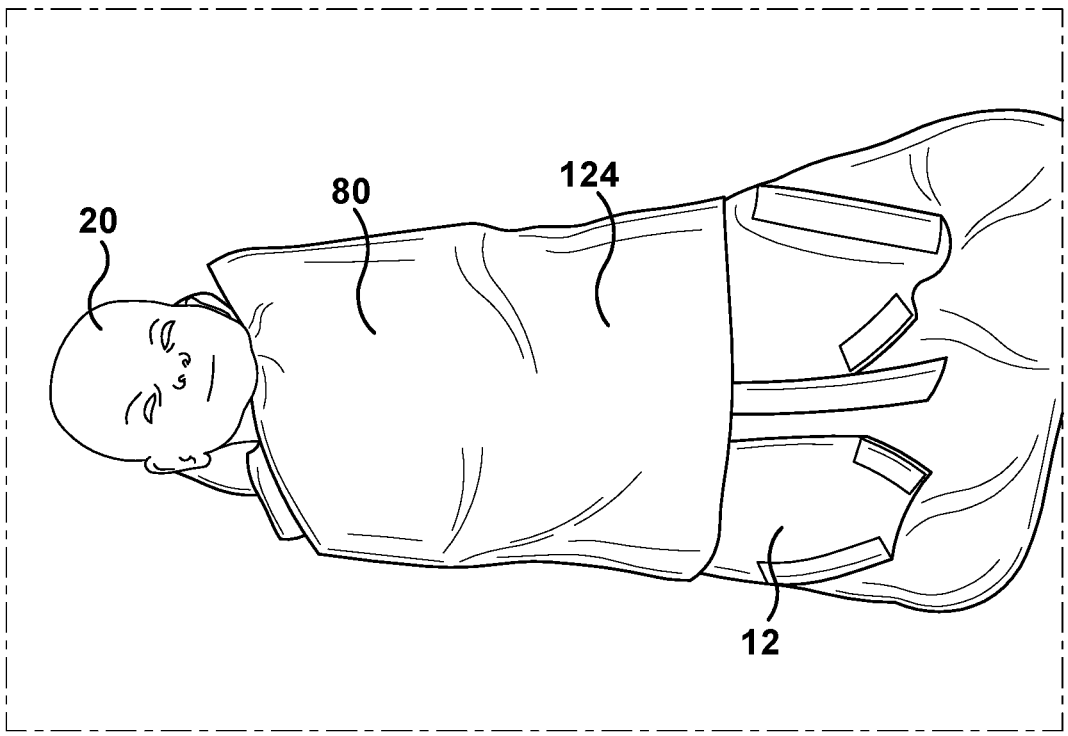

As shown in FIGS. 12 and 13, the sack 100 may further include a front surface 114 and a back surface 116. The front surface 114 includes an opening 118 and a closure mechanism 120 configured to close the opening 118 of the front surface 114. The opening 18 may be used to place the infant 20 into the sack 100. The closure mechanism 120 may take the form of any suitable structure for keeping the opening 118 closed. For example, the closure mechanism 120 may comprise one or more of snaps, buckles, Velcro, clips, adhesive strips, a zipper, and/or ties.

Turning to FIGS. 14-17, the flexible garment 12 may additionally include a wrap 80 configured to be wrapped around and swaddle the infant 20. The wrap 80 includes a top surface 124 located opposite a bottom surface 126. The bottom surface 126 of the wrap faces towards the infant 20 when the infant is received in the flexible garment 12 and when the infant 20 is swaddled by the wrap 80. The bottom surface 126 has a first fastener 130 and the top surface 124 has a second fastener 132 configured to releasably engage with the first fastener 130. As will be understood by one of ordinary skill in the art, the first and second fasteners 130, 132 may take the form of any suitable structure for maintaining the position of the wrap 80. For example, the first and second fasteners 130, 132 may comprise one or more of snaps, buckles, Velcro, clips, adhesive strips, a zipper, and/or ties.

The wrap 80 may releasably attach to the sack 80 via a third fastener 140. The third fastener 140 may take the form of any suitable structure for securing the wrap 80 to the sack 80. For example, the third fastener 140 may comprise one or more of snaps, buckles, Velcro, clips, adhesive strips, a zipper, and/or ties.

To reduce the amount of light emitted by the light emitting pads 14 that escapes from the flexible garment 12 in a direction away from the infant 20, the wrap 80 may be at least partially opaque to light emitted by the at least one light emitting pad 14 received by the pocket 82. For example, the wrap 80 may be at least 50%, 70%, 85%, or 90% opaque to light having a wavelength of 450 nm.

Figure 18:
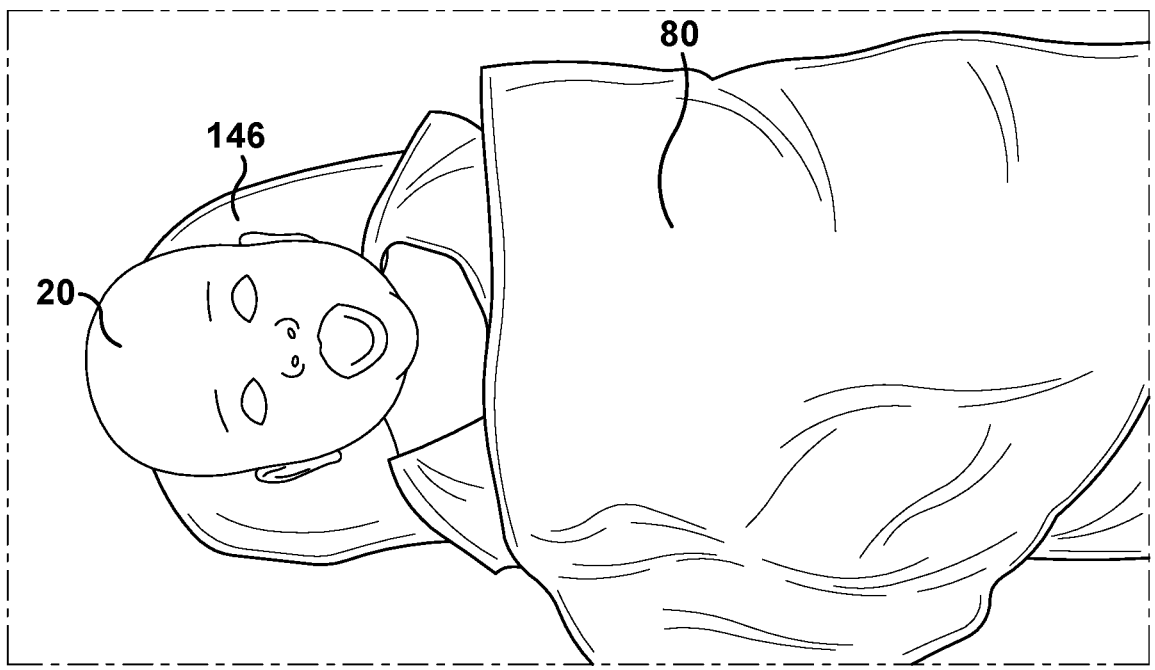
FIG. 18 shows a contoured portion of the wrap of the flexible garment.

As shown in FIG. 18, the wrap 80 may be contoured such that, when the infant 20 is swaddled by the wrap 80, an edge 136 of the wrap 80 nearest to and directly below a chin of the infant 20 dips away from the chin of the infant 20. The contour of the wrap 80 and the arm holes 110 prevent the wrap 80 and the sack 100 from covering a mouth of the infant 20 when the infant 20 is received in the flexible garment 12 and the infant 20 is swaddled by the wrap 80. The contour of the wrap 80 may take any suitable form that dips away from the chin of the infant 20.

Figure 19:
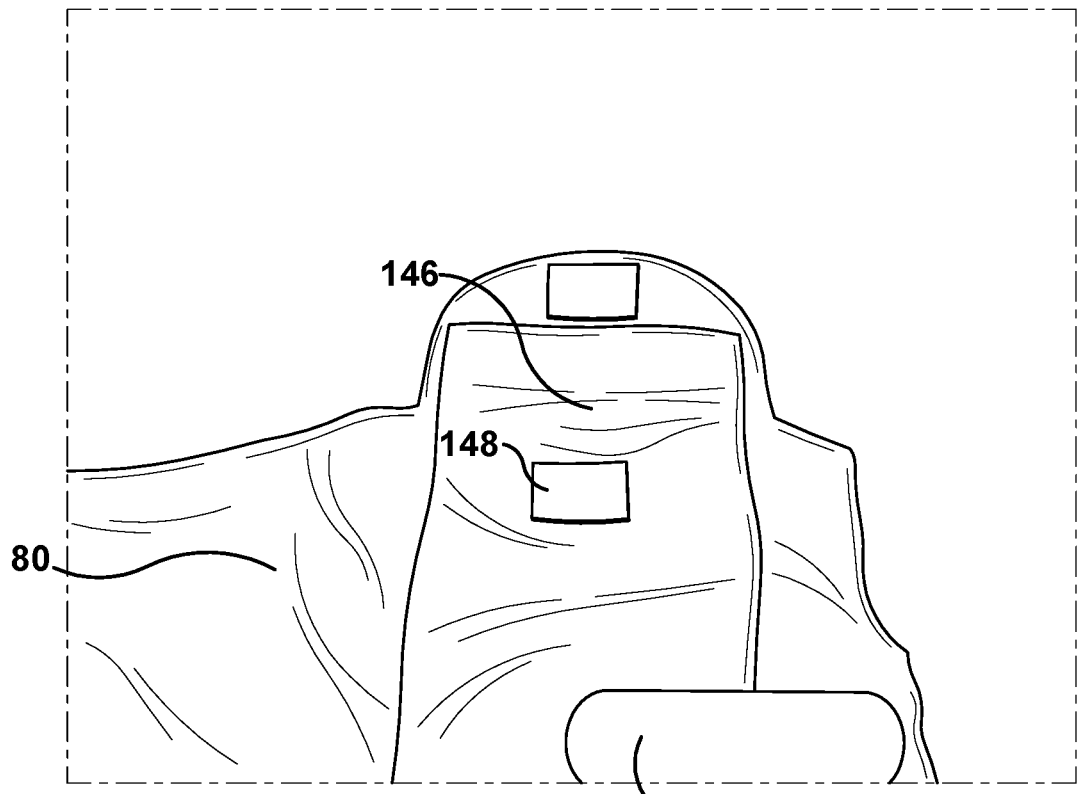
FIGS. 19 and 20 show the back surface of the flexible garment including the head piece.
Figure 20:
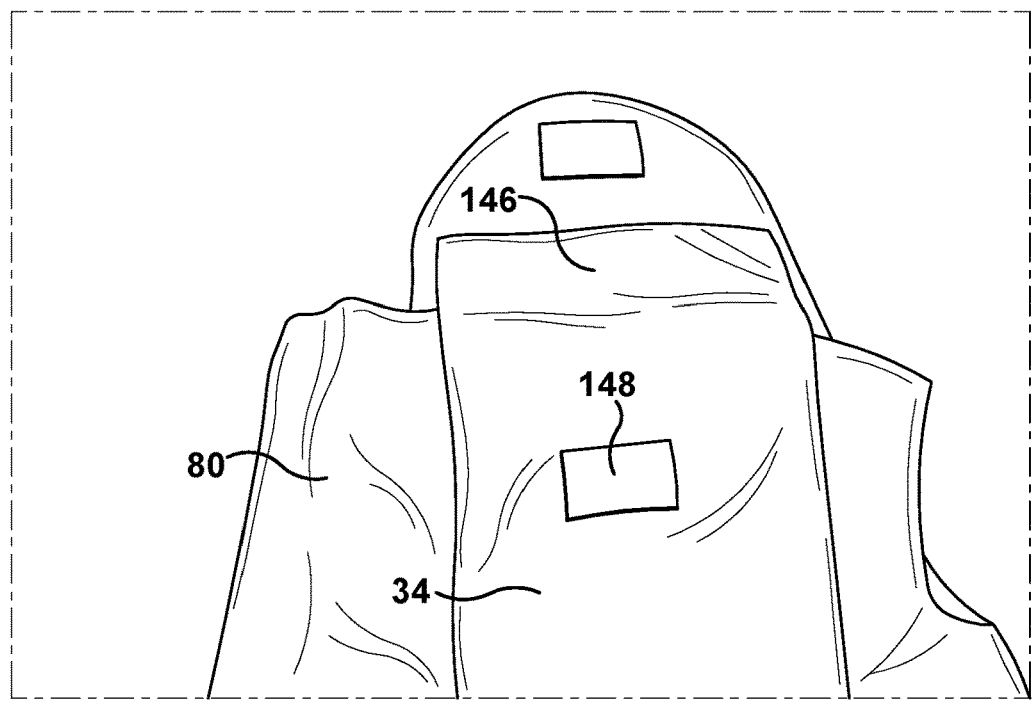
Figure 21:
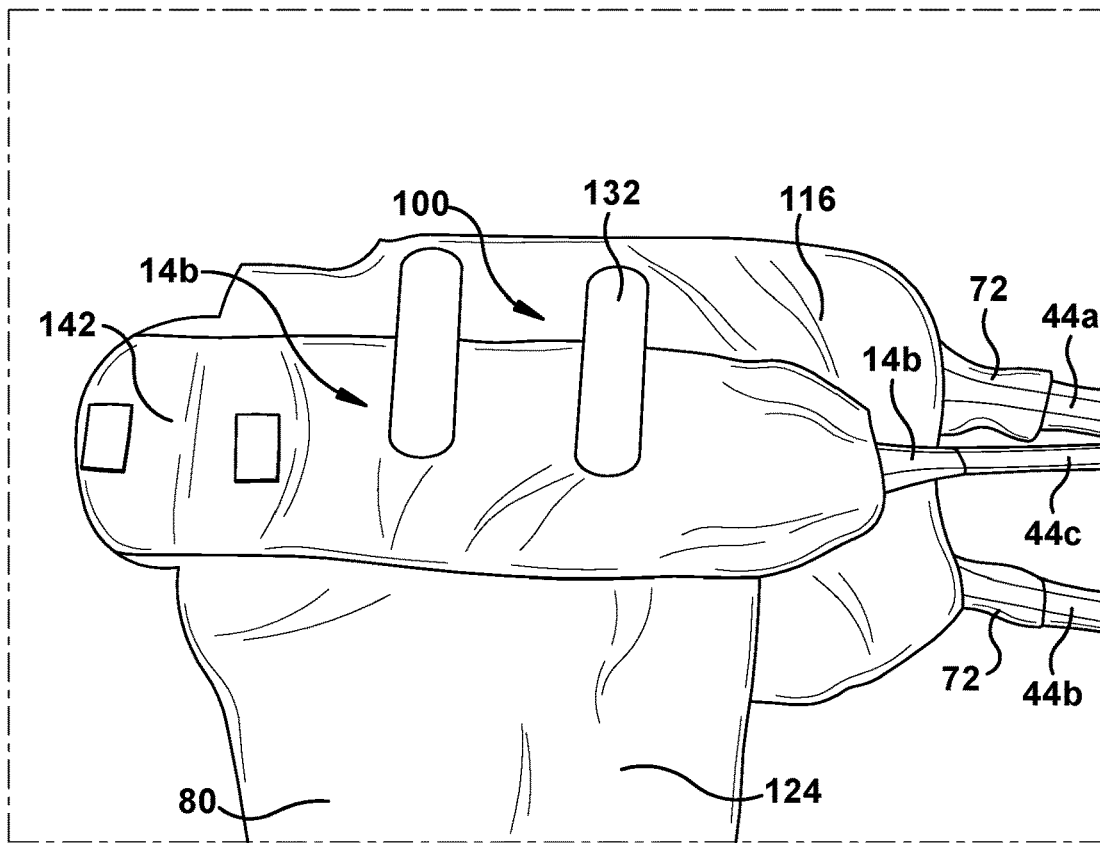
FIG. 21 is an exemplary embodiment of the phototherapy device including three light emitting pads.

Turning to FIGS. 19-21, the phototherapy device 10 may also include a head piece 142. The head piece 142 may be used as part of applying phototherapy to a neck and back of the head of the infant 20. Light may be supplied to the neck and head of the infant 20 by the bottom light emitting pad 14*b*. That is, the bottom light emitting pad 14*b* may include a head light emitting pad 144. The head light emitting pad 144 may be a separate light emitting pad 14 or may comprise a portion of the back light emitting pad 14*b*. For example, if a separate light emitting pad 14, the head light emitting pad 144 may be separately connected to the connector 16 via a different branch 44 than the back light emitting pad 14*b*.

The head piece 142 includes a compartment 146 for receiving the head light emitting pad 144. The compartment 146 may be a portion of the back pocket 82*b*. Alternatively, the head piece 142 may be a separate component that is attached to the flexible garment 12. For example, the head piece may include a fourth fastener 148 for releasably attaching the head piece 142 to the flexible garment 14. In this example, the compartment 146 may be separate from the back pocket 82*b*. For example, when separate from the back pocket 82*b*, the head light emitting pad 144 may be separate from the back light emitting pad 14*b*.

Figure 22:
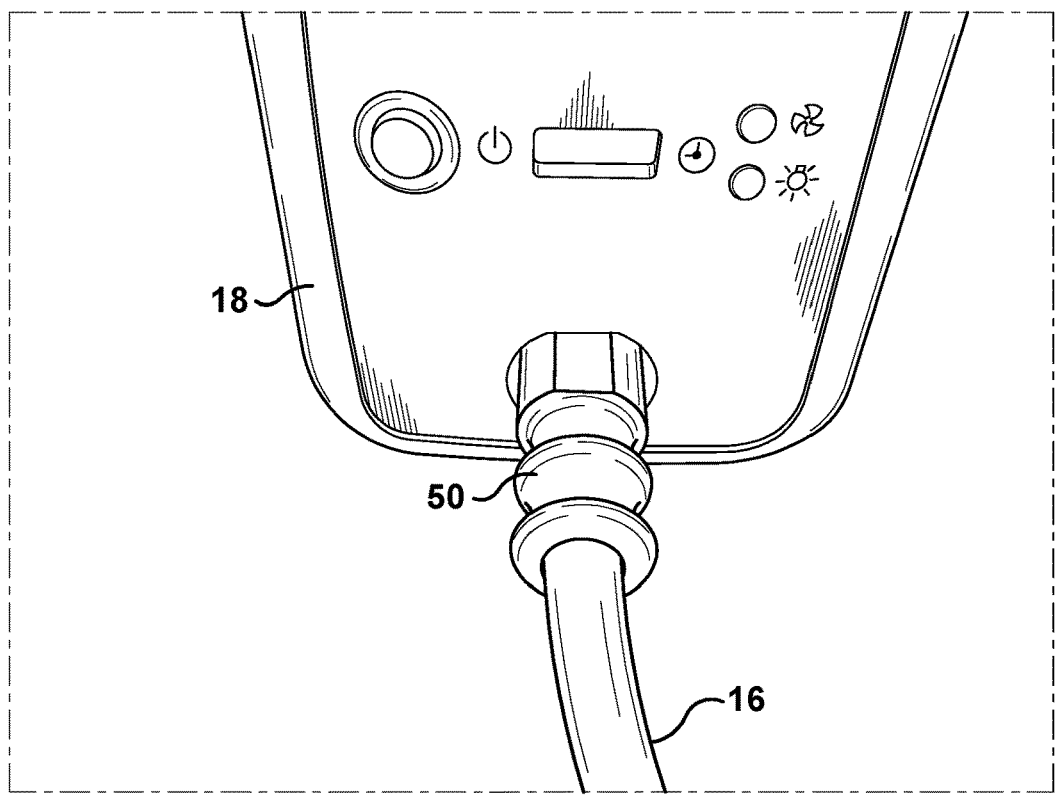
FIG. 22 is a front view of a light source.
Figure 23:
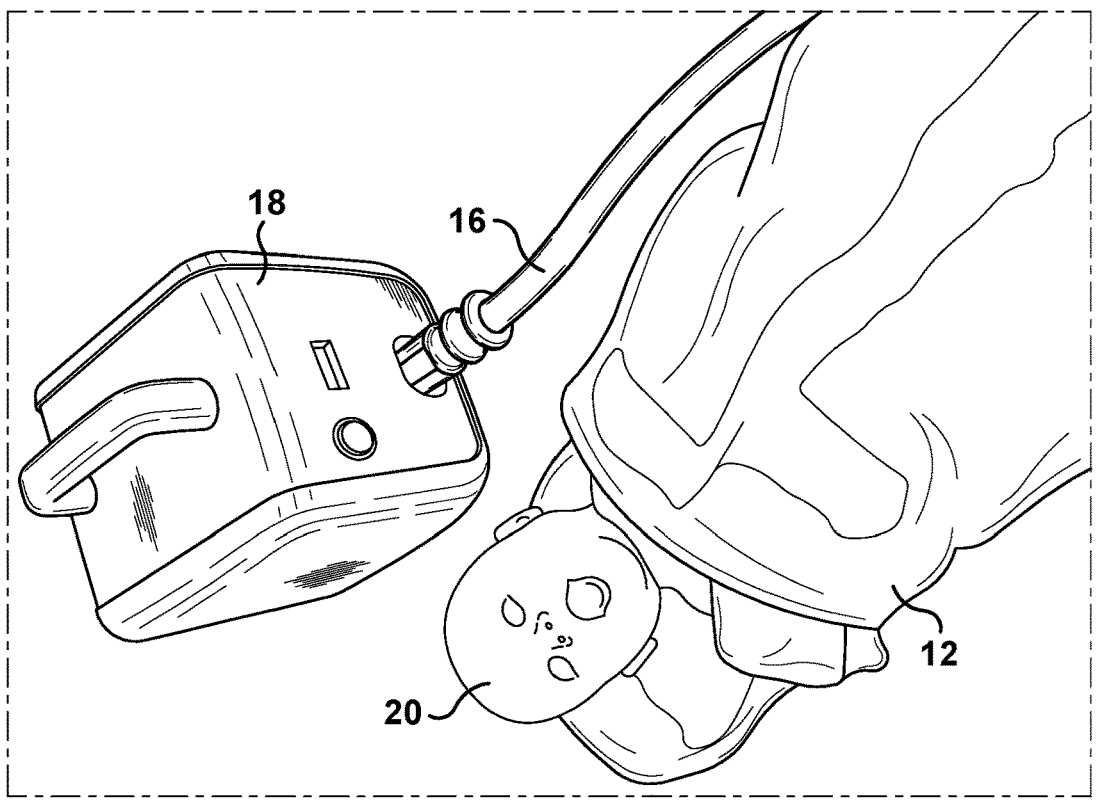
FIG. 23 shows the phototherapy device connected to the light source with the light emitting pads emitting light.

Turning to FIGS. 22 and 23, the light emitting pads 14 may be optically connected to a single output port 40 of the light source 18. The light emitting pads 14 receive light from the single output port 40 of the light source 18 via the connector. As shown in FIG. 24, the connector 16 includes a light guide 42 having multiple branches 44. Each of the branches 44 terminates in a respective one of the light emitting pads 14. As will be understood by one of ordinary skill in the art, while the embodiments depicted in this application show three light emitting pads 14, the phototherapy device 10 may include any suitable number of light emitting pads 14. For example, the phototherapy device 10 may include two, three, four, or five light emitting pads 14. Each of the light emitting pads 14 may be received in a corresponding pocket 82. Each pocket 82 may receive one or more of the light emitting pads 14.

As shown in FIG. 25, the light emitting pads 14 may include a light emitting material 70 protected by a cover 72 that is (at least partially) transparent to light emitted by the at least two discrete light emitting pads 14. As an example, the light emitting pads 14 may be formed from distal end portions 24 of the light guide 42 arranged in a planar structure configured to emit light via a light emitting surface 66. For example, the light emitting pads 14 may comprise optical fibers in an arranged pattern (e.g., woven into a sheet) and/or a planar light guide. Each light emitting pad 14 may also include a back surface 74 and/or edges 76 that are opaque to light emitted by the at least two discrete light emitting pads 14. The light emitting pads may additionally include a reflector 68 positioned opposite the light emitting surface 66. The reflector 68 is configured to reflect towards the light emitting surface 66 at least one wavelength of light emitted by the light source 18.

Figure 26:
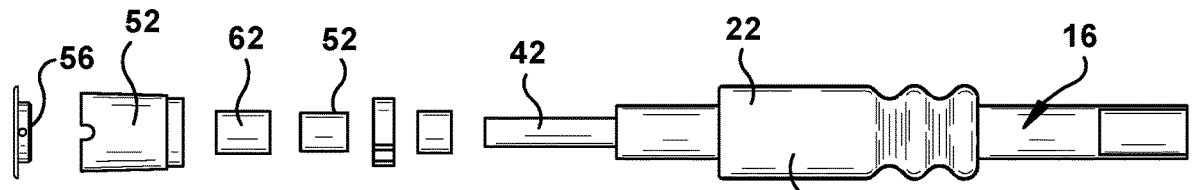
FIG. 26 is an exploded view of a coupler of the connector.

Turning to FIG. 26, the light guide 42 may include a plurality of optical fibers 46 and a ferrule 52 binding the optical fibers 46. The connector 16 may include a housing that extends along the length of and protects the light guide 42. The connector 16 may include a coupler 50 that directly interfaces with the light source 18. As light emitted by the light source 18 enters the connector 16, heat is generated near the coupler 50 and/or ferrule 52. If this heat is not removed, then the optical fibers 46 located near the coupler 50 may be damaged by the heat. For this reason, the coupler 50 may include a heat sink 54 thermally connected to the ferrule 52 and configured to draw heat away from the optical fibers 46.

The light guide 42 may be made of any suitable material having a structure, such that light emitted by the light source 18 and received by the connector 16 is propagated via total internal reflection along the light guide 42. For example, the light guide 42 may comprise a series of optical fibers (e.g., made from glass or plastic) extending approximately in parallel along the length of the light guide 42.

The coupler 50 may additionally include an end piece 56 having a magnetic material 62 configured to magnetically interact with a magnet 58 located near an output of the light source 18. In this way, the coupler 50 may be connected to the light source 18 with minimal effort on the part of a user. The heat sink 54 may be thermally connected to the end piece 56.

Figure 27:
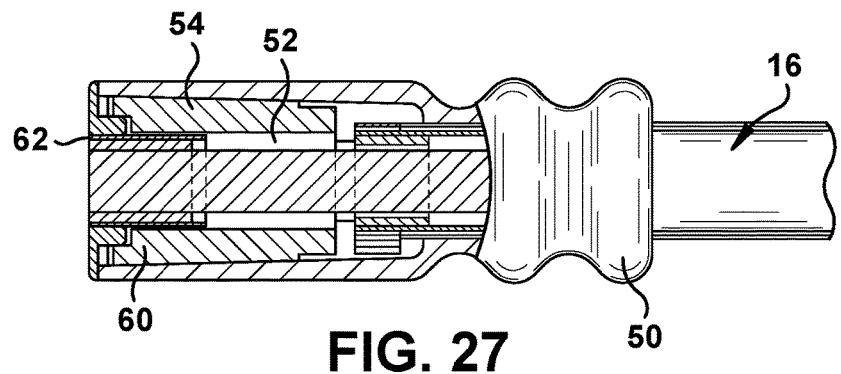
FIG. 27 is a partially transparent side view of the coupler.
Figure 28:
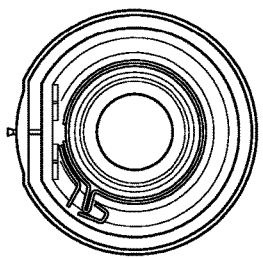
FIG. 28 is an end view of the coupler.

Turning to FIGS. 27 and 28, the heat sink 54 may have a non-magnetic material 60 thermally connected to the magnetic material 62, such that heat received by the magnetic material 62 is transferred to the non-magnetic material 60. As shown, the non-magnetic material 60 may have a larger mass and volume than the magnetic material 62. The magnetic material 62 may be steel and the non-magnetic material 60 may be aluminum. As will be understood by one of ordinary skill in the art, the magnetic material 62 may comprise any suitable magnetic material and is not limited to steel. Similarly, the non-magnetic material 60 is not limited to aluminum, but may comprise any suitable non-magnetic material 60.

Figure 29:
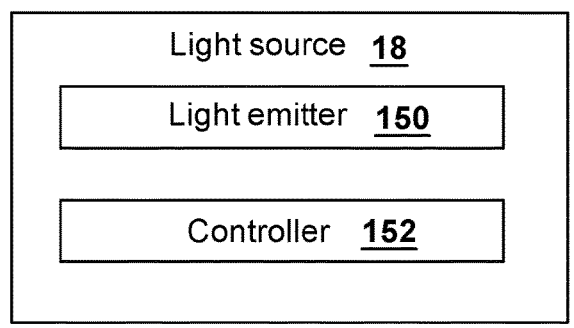
FIG. 29 is a schematic diagram of the light source.
Figure 30:
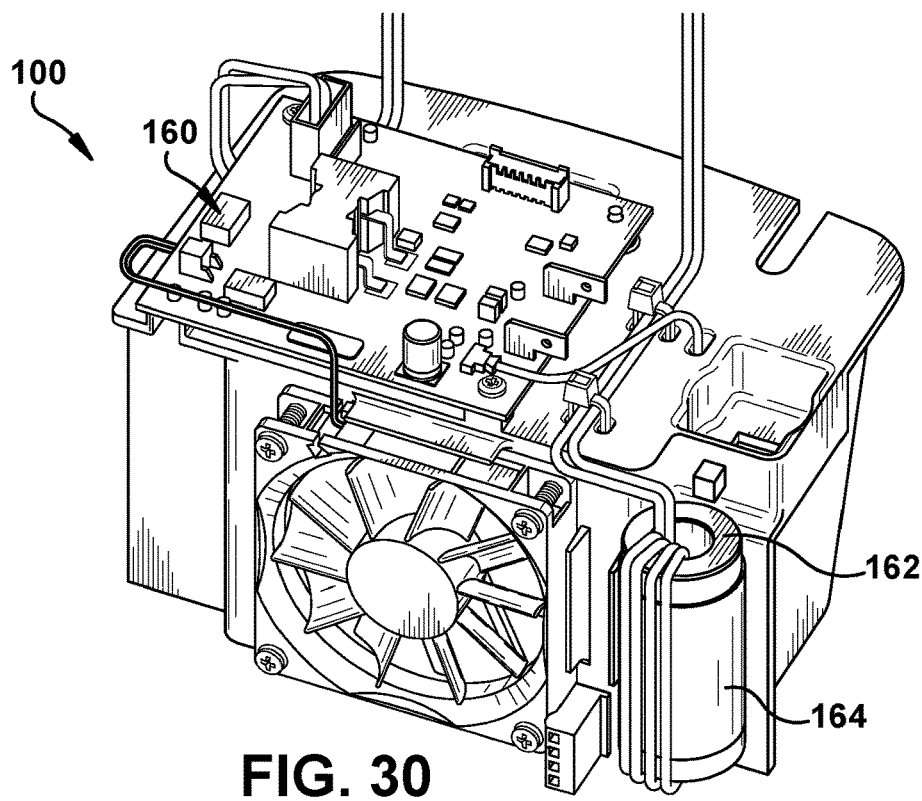
FIGS. 30-32 are schematic diagrams of internal components of the light source.
Figure 31:
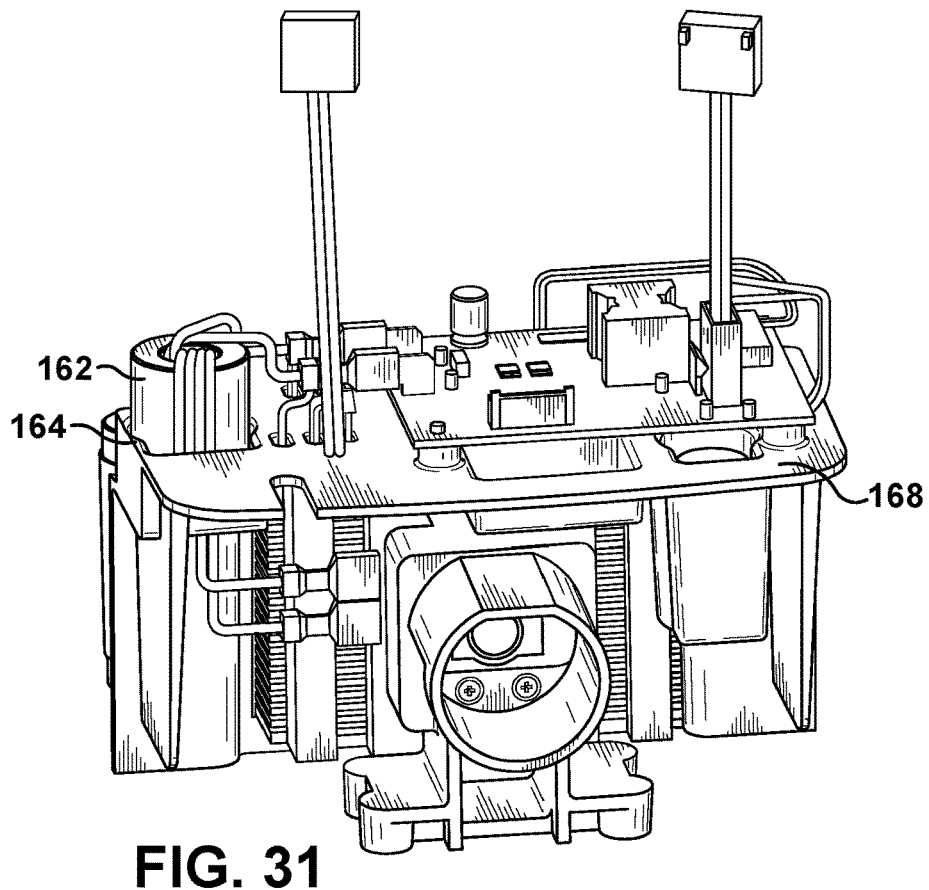
Figure 32:
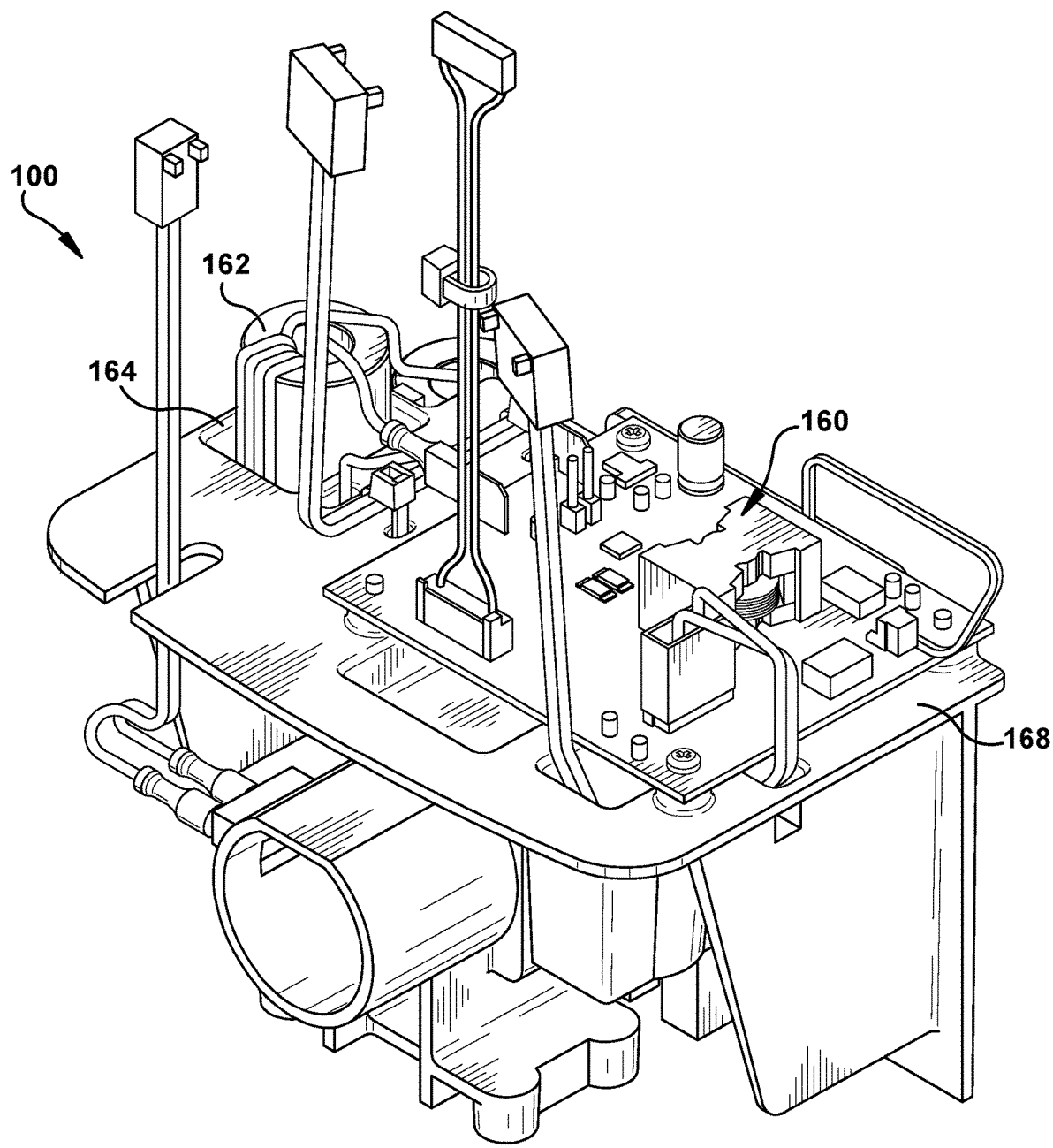

As shown in FIG. 29, the light source 18 includes a light emitter 150 and a controller 152. The light emitter 150 may comprise any suitable light emitter, incandescent, halogen, xenon, metal-halide, light emitting diodes (LED) (including organic light emitting diodes (OLED) and polymer light emitting diodes (PLED)), and fluorescent. As an example, the light emitter 150 may be at least one LEDs. The controller 152 is configured to modulate the dosage of light delivered to the infant 20 via the pads 14. For example, the light source 18 may include a sensor configured to directly measure the amount of light being emitted by the light source 18. Alternatively, the light source 18 may estimate the amount of light being emitted by the light source 18 based on measured properties of the light source 18 (e.g., temperature, current, etc.). The light source 18 may use the measured/estimated amount of light being emitted as a feedback to adjust the operating parameters of the light emitter 150 to control the dosage of light being emitted by the light source 18. For example, the controller 152 may be configured to modulate the dosage to provide a therapeutically effective dose to treat jaundice in the infant 20.

Turning to FIGS. 29-32, the light source 18 includes electrical components 160 that generate electromagnetic interference. For example, the electrical components 160 may include the controller 152, the circuitry providing power to the light emitter 150 and the controller 152, etc. The light source 18 may also include inductors 162 and positioners 164. Each positioner 164 is configured to receive one of the inductors 162 and maintain a position of the received inductor 162 at a location relative to a particular electrical component 160 of the electrical components 160. The position is maintained such that the electromagnetic interference generated by the particular electrical component 160 is absorbed by the received inductor 162. In this way, the combination of the inductors 162 and positioners 164 act in concert to reduce the electromagnetic interference generated by the electrical components 160 of the light source 18. For example, the inductor 162 may reduce the emission of electromagnetic interference by the electrical components 160 by at least 20%, 40%, 50%, 75%, 90%, or o5%. As will be understood by one of ordinary skill in the art, while the inductors 162 and positioners 164 are described as part of the light source 18, the inductors 162 and positioners 164 may be used to absorb the electromagnetic interference generated by electrical components 160 in any device.

The light source 18 may also include a structural support 168 for the electrical components 160. Each positioner 164 may comprise a molded piece integrated into the structural support 168 for the electrical components 160.

Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A phototherapy device for delivering light emitted by a light source to an infant, the device including:
at least two discrete light emitting pads including a front light emitting pad and a back light emitting pad, wherein the at least two discrete light emitting pads are configured to collectively be optically connected to a single output port of the light source via a connector comprising:
a light guide including multiple physically separated branches each terminating in a respective one of the two discrete light emitting pads, such that the light emitted by the light source is:
received at a proximal end of the connector,
propagated through the connector to each of the at least two discrete light emitting pads, and
emitted by each of the at least two discrete light emitting pads; and
a flexible garment configured to receive the infant and including at least two pockets each configured to separately receive and maintain the position of at least one of the light emitting pads relative to the infant, wherein:
the flexible garment includes a front side, a back side, a closed bottom edge opposite a partially closed top between the front side and the back side, arm holes located between the front side and the back side, and a wrap configured to be wrapped around and swaddled the infant;

the front side of the flexible garment is configured to be located adjacent a chest of the infant when the infant is received in the flexible garment;

the front side of the flexible garment comprises a front left side, a front right side an opening between the front left side and front right side, and a closure mechanism configured to close the opening on the front side to secure the infant in the flexible garment;

the at least two pockets include a front pocket having an internal space formed on the front left side of the front side of the flexible garment or the front right side of the front side of the flexible garment and a back pocket having an internal space formed on the back side of the flexible garment;

the back side of the flexible garment is configured to be located adjacent a back of the infant when the infant is received in the flexible garment;

a position of the front light emitting pad is maintained by the front pocket on the front side of the flexible garment when the front light emitting pad is received by the flexible garment, such that the front light emitting pad is located adjacent a chest of the infant;

the arm holes are configured such that arms of the infant extend through the arm holes when the infant is received in the flexible garment, such that the light emitted by the front light emitting pad is not obstructed by the arms of the infant before reaching the chest of the infant;

a position of the back light emitting pad is maintained by the back pocket on the back side of the flexible garment when the back light emitting pad is received by the flexible garment;

the internal space of the front pocket is separate and distinct from the internal space of the back pocket;

each of the multiple separated branches of the light guide are repositionable relative to other branches of the multiple separated branches of the light guide, such that the front light emitting pad is positionable within the internal space of the front pocket simultaneously with the back light emitting pad positioned within the separate internal space of the back pocket, and the front pocket and the back pocket are configured for insertion of the respective front light emitting pad and back light emitting pad from an end the flexible garment opposite the closed top of the flexible garment.

2. The device of claim 1, wherein the light guide includes a plurality of optical fibers and the connector further comprises a coupler configured to directly interface with the light source, the coupler including:
a ferrule binding the optical fibers; and
a heat sink thermally connected to the ferrule for drawing heat away from the optical fibers.

3. The device of claim 2, wherein:
the coupler additionally includes an end piece comprising a magnetic material configured to magnetically interact with a magnet located near an output of the light source; and
the heat sink is thermally connected to the end piece.

4. The device of claim 3, wherein the heat sink comprises a non-magnetic material thermally connected to the magnetic material, such that heat received by the magnetic material is transferred to the non-magnetic material.

5. The device of claim 1, wherein the light emitting pads are formed from distal end portions of the light guide arranged in a planar structure configured to emit light via a light emitting surface.

6. The device of claim 5, wherein the light emitting pads additionally include a reflector positioned opposite the light emitting surface and the reflector is configured to reflect towards the light emitting surface at least one wavelength of light emitted by the light source.

7. The device of claim 1, wherein the at least two light emitting pads comprise a light emitting material protected by a cover that is transparent to light emitted by the at least two discrete light emitting pads.

8. The device of claim 1, wherein each of the at least two discrete light emitting pads includes a back surface and/or edges that are opaque to light emitted by the at least two discrete light emitting pads.

9. The device of claim 1, wherein the flexible garment comprises a flexible cover configured to wrap around the infant.

10. The device of claim 1, wherein each of the at least two pockets:
include an outer wall and an inner wall located opposite the outer wall;
the inner wall is positioned between the infant and the at least one light emitting pad received by the pocket; and
the inner wall is at least partially transparent to light emitted by the at least one light emitting pad received by the pocket.

11. The device of claim 1, wherein the flexible garment includes a sack comprising:
a closed bottom edge;
a partially closed top including a hole through which a neck of the infant extends when the infant is received in the flexible garment; and
two partially closed sides including the arm holes through which arms of the infant extend when the infant is received in the flexible garment.

12. The device of claim 11, wherein the sack further includes:
a front surface and a back surface, wherein the front surface includes an opening and a closure mechanism configured to close the opening of the front surface.

13. The device of claim 11, wherein:
the flexible garment additionally includes a wrap configured to be wrapped around and swaddle the infant;
the wrap includes a top surface located opposite a bottom surface;
the bottom surface of the wrap faces towards the infant when the infant is received in the flexible garment and when the infant is swaddled by the wrap;
the bottom surface has a first fastener; and
the top surface has a second fastener configured to releasably engage with the first fastener.

14. The device of claim 13, wherein:
the wrap is contoured such that, when the infant is swaddled by the wrap, an edge of the wrap nearest to and directly below a chin of the infant dips away from the chin of the infant;
the contour of the wrap and the arm holes prevent the wrap and the sack from covering a mouth of the infant when the infant is received in the flexible garment and the infant is swaddled by the wrap.

15. The device of claim 1, further comprising a head piece, wherein:
the bottom light emitting pad includes a head light emitting pad;

the head piece includes a compartment for receiving the head light emitting pad.

16. The device of claim 15, wherein the head light emitting pad comprises a portion of a back light emitting pad.

17. The device of claim 1, wherein:
the at least two discrete light emitting pads comprise three light emitting pads;
the three light emitting pads include a front right light emitting pad, a front left light emitting pad, and a back light emitting pad;
the flexible garment includes:
a front side and a back side;
three distinct and separate pockets comprising a front left pocket located on the front left side of the flexible garment, a front right pocket located on the front right side of the flexible garment, and a back pocket located on the back side of the flexible garment, wherein:
a position of the front left light emitting pad is maintained by the garment on the front left side of the flexible garment by the front left pocket when the front left light emitting pad1 is received by the flexible garment;
a position of the front right light emitting pad is maintained by the garment on the front right side of the flexible garment by the front right pocket when the front right light emitting pad is received by the flexible garment; and
a position of the back light emitting pad is maintained by the garment on the back side of the flexible garment by the back pocket when the back light emitting pad is received by the flexible garment.

18. The system comprising: the phototherapy device of claim 1, a light source including at least one light emitting diode LED), wherein the light source includes electrical components that generate electromagnetic interference; and inductors and positioners;
each positioner is configured to:
receive one of the inductors;
maintain a position of the received inductor at a location relative to a particular electrical component of the electrical components, such that the electromagnetic interference generated by the particular electrical component is absorbed by the received inductor.

19. The system of claim 18, further comprising a structural support for the electrical components, wherein each positioner comprises a molded piece integrated into the structural support for the electrical components.

20. A flexible garment configured to receive an infant and at least two discrete light emitting pads and maintain a position of the at least two discrete light emitting pads relative to the infant, including a front light emitting pad and a back light emitting pad, the flexible garment comprising: a front side configured to be located adjacent a chest of the infant when the infant is received in the flexible garment; a back side configured to be located adjacent a back of the infant when the infant is received in the flexible garment;

the front side of the flexible garment comprises a front left side, a front right side, an opening between the front left side and front right side, and a closure mechanism configured to close the opening on the front side to secure the infant in the flexible garment; the at least two pockets include a front pocket having an internal space formed on the front left side of the front side of the flexible garment or the front right side of the front side of the flexible garment and a back pocket having an internal space formed on the back side of the flexible garment;

and the front pocket and the back pocket are configured for insertion of the respective front light emitting pad and back light emitting pad from an end of the flexible garment opposite the closed top of the flexible garment at least two pockets comprising a front pocket located on the front side of the flexible garment and a back pocket located on the back side of the flexible garment, wherein: each of the at least two pockets: are configured to receive and maintain a position of at least one of the light emitting pads; include an outer wall and an inner wall located opposite the outer wall; the inner wall is positioned between the infant and the at least one light emitting pad received by the pocket; and the inner wall is at least partially transparent to light.

* * * * *